United States Patent [19]

Webster

[11] 4,260,262

[45] Apr. 7, 1981

[54] GRAIN QUALITY ANALYZER

[75] Inventor: Donald R. Webster, Laurel, Md.

[73] Assignee: Neotec Corporation, Silver Spring, Md.

[21] Appl. No.: 964,191

[22] Filed: Nov. 28, 1978

[51] Int. Cl.³ .......................................... G01N 21/27
[52] U.S. Cl. .................................. 356/418; 356/446; 356/448; 364/526
[58] Field of Search ................. 356/51, 416, 418, 419, 356/433, 434, 445, 446, 448; 364/498, 526

[56] References Cited

U.S. PATENT DOCUMENTS

| | | | |
|---|---|---|---|
| 3,765,775 | 10/1973 | Ganssle et al. | 356/418 |
| 3,776,642 | 12/1973 | Anson et al. | 356/418 |
| 3,828,173 | 8/1974 | Knepler | 356/418 X |
| 3,861,788 | 1/1975 | Webster | 356/418 X |
| 3,877,818 | 4/1975 | Button et al. | 356/445 X |
| 4,037,970 | 7/1977 | Webster et al. | 356/418 |
| 4,082,464 | 4/1978 | Johnson, Jr. | 356/418 |

*Primary Examiner*—F. L. Evans
*Attorney, Agent, or Firm*—Lane, Aitken, Ziems, Kice & Kananen

[57] ABSTRACT

An improved grain quality analyzer, for analyzing the percentage concentration of various constituents, e.g. protein and water, in a grain sample, photo-optically measures the change in the optical density of the sample, Δ OD, in a range of characteristic wavelengths and, for protein, in a range of neutral wavelengths and uses these measured values to compute the percentage concentration of the constituents.

A grain sample is irradiated with light, the wavelength of which sweeps across the infrared light-spectrum including a range of wavelengths termed characteristic wavelengths, and, for protein, a range of wavelengths termed neutral wavelengths. The characteristic wavelengths are those wavelengths at which the optical characteristics of the irradiated sample, that is, the optical density, reflectivity, transmissivity, and/or absorption, are known to vary as a function of the concentration of the measured constituent, and, for the protein measurement, the neutral wavelengths are those wavelengths at which the optical characteristics are substantially independent of the concentration of the protein.

In the preferred embodiment, photo-optical sensors measure the light reflected from the sample and provide output signals indicative of the optical density of the sample as a function of the wavelength of the irradiating light. Control and computing means sample the sensor output at spaced apart points in the range of characteristic wavelengths and in the range of neutral wavelengths to provide signals representative of the optical characteristics of the sample. Computing circuitry computes the percentage concentration of water and, for protein, computes the percentage concentration using an algorithm in accordance with the present invention which eliminates the inaccuracies introduced by light scattering from the sample.

13 Claims, 6 Drawing Figures

GRAIN QUALITY ANALYZER

CROSS REFERENCE TO RELATED PATENTS

The subject matter of this patent application is related to the subject matter of U.S. Pat. No. 3,861,788, issued Jan. 21, 1975 to Donald R. Webster; U.S. Pat. No. 4,082,464, issued Apr. 4, 1978 to Robert L. Johnson; and U.S. Pat. No. 4,037,970 issued July 26, 1977 to Donald R. Webster and Eugene R. Ganssle, all three of which are assigned to the assignee of the present invention. The disclosures of these patents are incorporated herein to the extent necessary to practice the present invention.

BACKGROUND OF THE INVENTION

The present invention relates to an improved grain quality analyzer and, more particularly, to a grain quality analyzer which includes photo-optical means for measuring the optical characteristics of a sample, and control and computing means for computing the percentage concentration of selected constituents in the grain sample.

The value of agricultural grain commodities, such as wheat, corn, soy beans, and the like, from both the economic and nutritional standpoints, is partly determined by the percentage concentration of protein and moisture. Consequently, it is desirable for those in the production, sale, and distribution of grains to have means for quickly and accurately measuring the percentage concentration of these constituents. It is known, for example, to determine these percentages by laboratory-type chemical analysis, an accurate but time consuming procedure, and by use of a photo-optical grain quality analyzer. Grain can be optically analyzed because certain optical characteristics of the grain, principally the optical density (OD), transmissivity, reflectivity, and absorption vary at certain wavelengths of light as a function of the concentration of protein, oil, and moisture.

A commercially available photo-optical grain quality analyzer is disclosed in the above referenced U.S. patents which are assigned to the assignee of the present invention. This instrument uses photo-optical techniques to obtain optical density values which are a function of the percentage concentrations of the protein, oil, and moisture and includes computation circuitry to compute the actual percentage concentration in accordance with known equations. A sample of the grain to be analyzed is irradiated with filtered light which passes from an infrared light source through a rotatable filter wheel to the grain sample. The filter wheel includes a plurality of radially extending filters, each of which is designed to pass light at a selected wavelength. As the filter wheel rotates, each filter is successively introduced into the irradiating light and caused to pass filtered light energy at wavelengths which sweep across a selected bandwidth from a first wavelength to a second wavelength in the infrared spectrum. The cumulative effect of the plural filters of the filter wheel is to irradiate the sample with light, the wavelength of which sweeps, in serially adjacent bandwidths, across a substantial portion of the infrared spectrum. The irradiating light includes selected wavelengths which are known to be of value in determining the percentage concentration of the measured constituents and, specifically, are those light wavelengths at which the optical characteristics of the sample, viz., the optical density (OD), reflectivity, transmissivity, and/or absorption, are known to vary as a function of the concentration of the measured constituent. In the reflectance mode of operation, photo-responsive devices are positioned with respect to the sample such that they measure the light reflected from the sample as the wavelength varies. This reflected light, which is inversely proportional to the optical density (OD) of the sample, is used to provide a measure of the optical density of the sample at a selected wavelength and a measure of the change in the optical density (that is, the $\Delta OD$) as the wavelength of the light is swept across the infrared spectrum.

The above described grain quality analyzer employs equations relating to the non-destructive photo-optical testing of agricultural products in which the reflective optical density is measured by the reflectivity R and is defined by the following equation:

$$OD = \text{Log}(1/R) \qquad \text{EQ. 1}$$

In this equation, the reflectivity, R, is a ratio of the intensity of the reflected light to the intensity of the incident light at the selected wavelength:

$$R = (I_r/I_i) \qquad \text{EQ. 2}$$

The change in the optical density between two wavelengths (that is, across a selected bandwidth) is given by the following equation:

$$\Delta OD = \text{Log}(I_i/I_r)_1 - \text{Log}(I_i/I_r)_2 \qquad \text{EQ. 3}$$

The subscripts 1 and 2 represent the first and second wavelengths. If the intensity of the irradiating light is approximately the same at both wavelengths, then the above equation reduces to:

$$\Delta OD = \text{Log}(I_r)_2 - \text{Log}(I_r)_1 \qquad \text{EQ. 4}$$

Consequently, the differences between the common log of the intensity of the reflected light is an indication of the change in the optical density.

The instrument employs control circuitry to obtain the $\Delta OD$ measurement at wavelengths which are known to vary as a function of the concentration of the protein, oil, and moisture and employs computational circuitry to compute the actual percentage concentration using the following three equations:

$$\text{oil \%} = K_0 + K_1(\Delta OD)_w + K_2(\Delta OD)_o + K_3(\Delta OD)_p \qquad \text{EQ. 5}$$

$$\text{water \%} = K_4 + K_5(\Delta OD)_w + K_6(\Delta OD)_o + K_7(\Delta OD)_p \qquad \text{EQ. 6}$$

$$\text{protein \%} = K_8 + K_9(\Delta OD)_w + K_{10}(\Delta OD)_o + K_{11}(\Delta OD)_p \qquad \text{EQ. 7}$$

In these three equations, K0-K11 are constants or "influence factors" and the subscripts W, O, and P indicate the characteristic wavelengths which are associated with the change in optical density measurements for these constituents. As indicated above, the characteristic wavelengths are those wavelengths at which the optical characteristics of the sample are sensitive to or vary with the percentage concentrations of water, oil, and protein.

The above described grain quality analyzer performs the necessary computations, both as to the $\Delta OD$ measurements and to the equations set forth above, by using electronic control and computation circuitry, including both analog and digital circuits. While the percentage concentration of the protein, oil, and moisture can be accurately determined, inaccuracies can occur because of the relatively large number of constants, $K_0$–$K_{11}$, which must be accurately determined and maintained in the computation circuitry, and the adverse effect of light scattering from sample to sample. The inaccuracies introduced into the measuring process by light scattering can be minimized, but not entirely eliminated, by preparing each grain sample in a consistent, uniform manner, e.g., by grinding the grain sample into uniformly sized particles.

Research efforts have been undertaken for the purpose of uncovering other, simpler equations for use in photo-optical instruments by which the percentages of the selected constituents can be photo-optically determined while maintaining or improving the accuracy of the measurement. One researcher, Mr. K. H. Norris, of the U.S.D.A. Agricultural Research Service in Greenbelt, Md., has empirically arrived at the following simplified equation for measuring the percentage concentration of protein in a grain sample:

$$\% P = K_0 + K_1 \frac{[R_1 - R_2/R_1 + R_2]_c}{[R_1 - R_2/R_1 + R_2]_n} \qquad \text{EQ. 8}$$

When compared to the protein equation employed by the above described grain quality analyzer (EQ.7), this equation utilizes two rather than four of the twelve influence factors and a reflectivity ratio obtained from the sample. The reflectivity values, $R_1$ and $R_2$, of the numerator and denominator represent, respectively, the reflectivity of the sample at two spaced points in the range of characteristic wavelengths and two spaced points in the range of neutral wavelengths. As explained above, the characteristic wavelengths for protein are a range of wavelengths in which the optical characteristics of the sample, in this case, the reflectivity, are sensitive to or vary as a function of the percentrage concentration of the protein, and the neutral wavelengths are those wavelengths at which the optical characteristics of the sample are not sensitive to or are independent of the percentage concentration of the measured constituent.

The use of a ratio of optical characteristics in determining the percentage concentration of a constituent was previously employed by Mr. Norris in photo-optically measuring the percentage contents of fat in ground meat as disclosed in U.S. Pat. No. 3,877,818, issued Apr. 15, 1975.

The present inventor, in an effort to further simplify the percentage protein determination, has derived a further equation which further simplifies the determination of the percentage protein and which is more compatible with less sophisticated, less expensive computational electronics.

SUMMARY OF THE INVENTION

In accordance with the present invention, an improved grain quality analyzer is provided for measuring the percentage concentration of selected constituents in a grain sample including water and protein. The analyzer includes means for irradiating a grain sample with light, the wavelength of which varies across a substantial portion of the infrared spectrum including a characteristic range of wavelengths for the water and protein and a protein neutral range of wavelengths.

Photo-optical sensors are positioned to receive light from a sample to provide signals representative of the reflectivity of the sample as the wavelength of the irradiating light sweeps across the characteristic and neutral wavelength ranges.

Instrument control circuits selectively measure and store the output of the sensors at various points in the infrared spectrum including, for the protein measurement, two spaced apart points in the protein characteristic range and two spaced apart points in the protein neutral range to provide signals indicative of the change in the optical density for protein in these two ranges.

Computing circuits responsive to the stored sensor signals compute the percentage concentrations of the water in accordance with known equations, and, for protein, the percentage concentration in accordance with the following equation:

$$\text{protein } \% = K_0 + K_1 \frac{\text{Log} \frac{1}{R_{1c}} - \text{Log} \frac{1}{R_{2c}}}{\text{Log} \frac{1}{R_{1n}} - \text{Log} \frac{1}{R_{2n}}} = \qquad \text{EQ. 9}$$

$$K_0 + K_1 \frac{\Delta OD_c}{\Delta OD_n}$$

This equation uses a ratio of the difference between the common logarithms of the optical density for the two spaced points in the protein characteristic range of wavelengths to the difference between the common logarithms of the optical density for the two spaced points in the protein neutral range of wavelentths.

The improved grain quality analyzer greatly reduces the inaccuracies introduced into the protein measurement by light scattering in the grain sample and permits computation of the percentage protein concentration using a simplified algorithm having less "influence factors" than the previously used protein equation and which is compatible with standard electronic computing elements.

It is a broad overall object of the present invention, among others, to provide an improved grain quality analyzer for quickly measuring and determining the percentage concentration of the selected constituent in a grain sample. Further objects of the present invention include providing an improved grain quality analyzer which uses photo-optical techniques to measure the percentage concentration of a selected constituent in a grain sample in which the effect of light scattering from sample to sample is eliminated and in which the computation of the percentage concentration of protein is effected by means of a simplified algorithm which is compatible with standard electronic computing elements.

BRIEF DESCRIPTION OF THE DRAWINGS

The above description, as well as further objects, features, and advantages, of the present invention will be more clearly appreciated by reference to the following detailed description of a presently preferred but nonetheless illustrative embodiment in accordance with the present invention, when taken in conjunction with the accompanying drawings wherein.

DESCRIPTION OF THE PREFERRED EMBODIMENT

Figure 1:
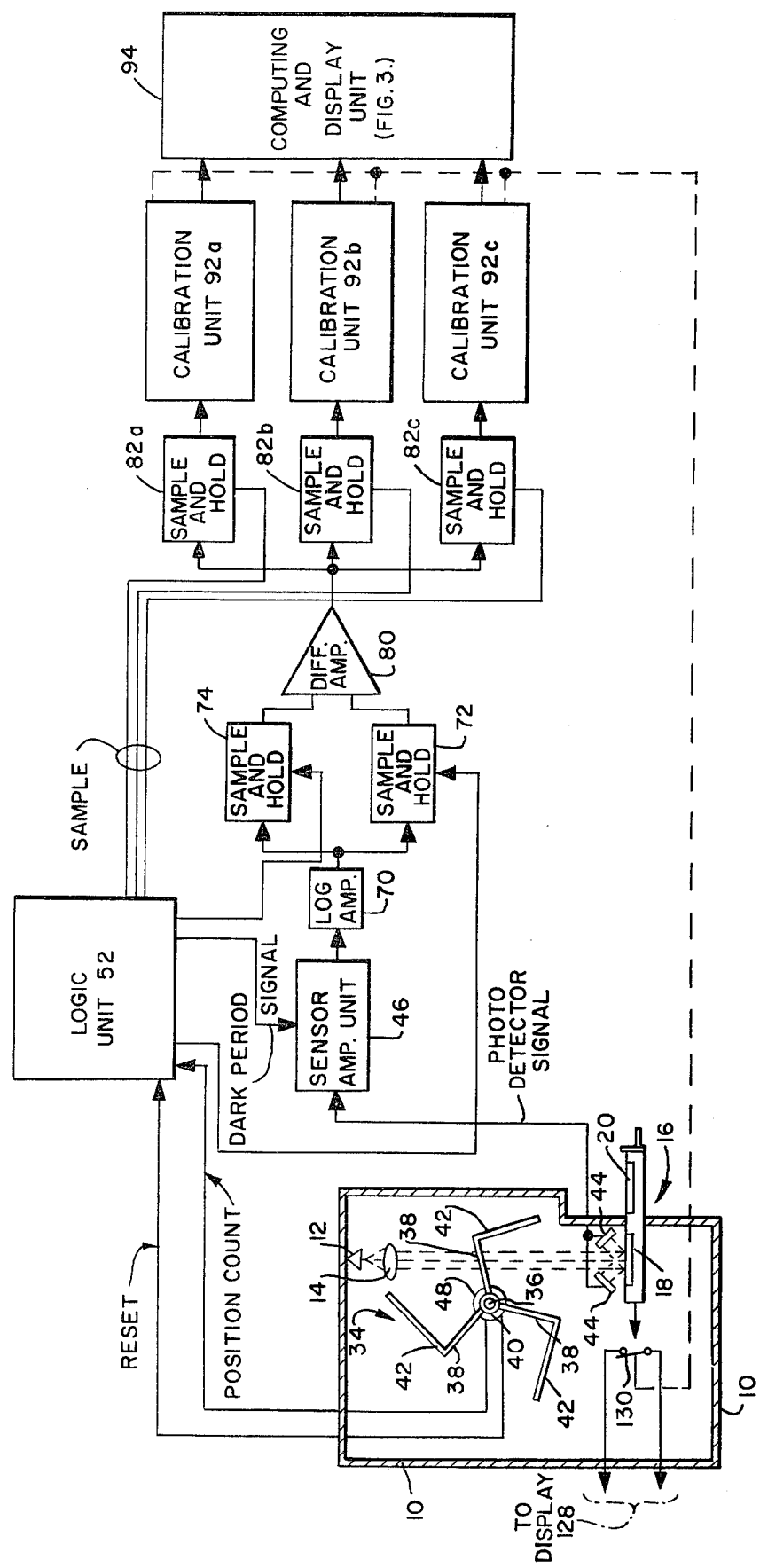
FIG. 1 is a schematic illustration of an exemplary grain quality analyzer and associated control and logic circuitry in accordance with the present invention.

A grain quality analyzer instrument in accordance with the present invention is shown in schematic form in FIG. 1 and includes a housing 10 and associated electronic control and computing elements. The housing 10 encloses and provides support for a lamp 12 and associated lens 14; a filter assembly 34, which is adapted to filter light emitted by the lamp 12; a movable sample drawer 16 positioned below the filter assembly 34 so as to be irradiated by filtered light; and a pair of photosensors 44 positioned above the sample drawer 16 to receive light energy reflected from the sample.

The lamp 12 is designed to emit high-intensity light energy across a wide band in the infrared spectrum. A portion of the emitted light is directed onto the lens 14, which collimates the light and directs it downwardly along an optical path (parallel broken lines) toward the filter assembly 34 and the sample drawer 16.

The sample drawer 16 includes two recesses or cavities 18 and 20 and is movable betwen an outward position, as shown in FIG. 1, in which the cavity 18 is positioned in the optical path so as to be irradiated with light emitted from the lamp 12 and an inward position in which the cavity 20 is positioned in the optical path to be similarly irradiated. The cavity 18 is intended to hold an instrument calibration standard to assist in establishing and maintaining the calibration of the analyzer, and the cavity 20 is designed to support a prepared grain sample for test in a sample holding cartridge as described in more detail in the aforementioned patents incorporated herein by reference.

The filter assembly 34 functions as a variable light filter which alternately filters and interrupts the irradiating light along the optical path. The filter characteristics are chosen such that the wavelength of the light during each irradiation period varies across a selected bandwidth in the infrared spectrum with the bandwidths preferably chosen such that they occupy adjacent regions in the infrared spectrum. Consequently, for each full revolution of the filter wheel, the sample drawer 16 is irradiated with light energy, the wavelength of which sweeps across a substantial portion of the infrared spectrum.

The filter assembly 34, in its preferred form, includes three plate-like filters 38, each of which is attached along a proximal edge to a support shaft 40. The filters 38 are located in planes which pass through the axis 36 of rotation and which are spaced 120° from one another. The distal edge of each filter 38 is connected to the edge of an opaque vane 42, each of which is located in a plane which, in the preferred form, is normal to the plane of its filter 38. The support shaft is adapted to be rotated in a clockwise direction as shown in FIG. 1 such that the vanes 42 alternately interrupt the collimated light along the optical path.

As the filter assembly 34 rotates, one of the vanes 42 will enter and interrupt the optical path to cut off or block the light incident on the sample drawer 16. With further rotation, the vane 42 moves out of the optical path with the associated filter 38 moving into the path to begin filtering the light. When the filter initially enters the incident light beam, it is disposed at an angle with respect to the optical path. As the filter assembly 34 continues its rotation, this angle changes until the plane of the filter 38 is substantially perpendicular to the optical path. Because of this change in the angular relationship between each filter 38 and the optical path, the filter, which is designed to pass light at a principal wavelength, passes light at wavelengths which continually vary as a function of the angular relationship between the filter and the optical path from a first wavelength to a second wavelength across a selected bandwidth. Thus, an essentially single wavelength filter can be used, in the filter assembly 34, to sweep light energy across a selected bandwidth in the infrared spectrum.

Figure 2:
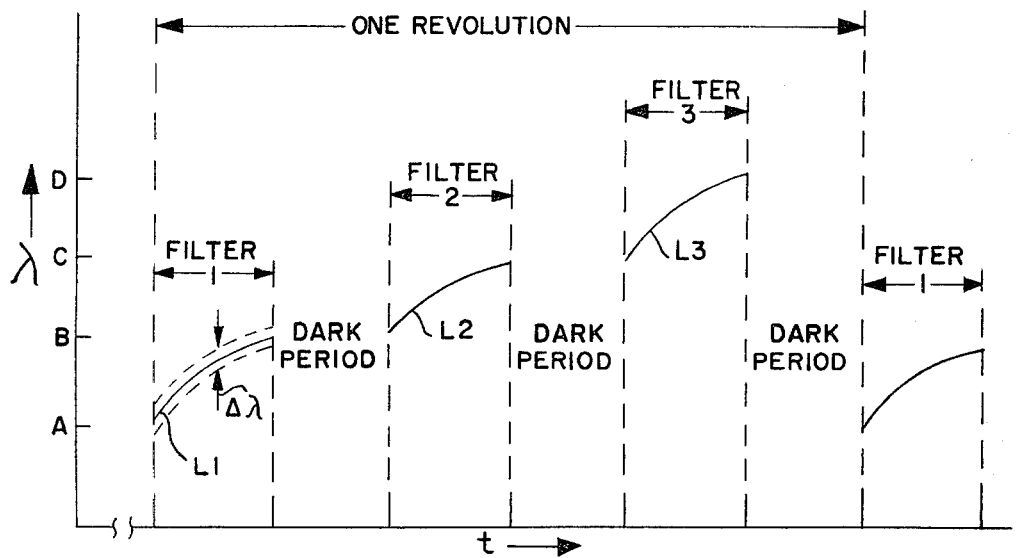
FIG. 2 is a graphical illustration of the characteristics of the light which irradiates the test sample in which the left vertical axis represents the wavelength of the irradiating light and the horizontal axis represents time.

The light energy incident on the sample drawer 16 is shown in graphical form in FIG. 2 with the horizontal axis representing time and vertical axis representing the wavelength of the light incident on the sample drawer 16. When a first filter 38 enters and rotates through the emitted light, the wavelength of the filtered light, represented by the solid line L1 in FIG. 2, sweeps from point A, when the plane of the filter 38 is at an angle with respect to the optical path, to point B, when the plane of the filter 38 is substantially perpendicular to the optical path of the emitted light. The two broken lines spaced from and on either side of the line L1 represent the tolerance in the wavelength which may be passed through the filter 38. At point B, when the filter is substantially perpendicular to the optical path, the vane 42 on the next successive filter 38 enters and interrupts the emitted light to cause, as shown in FIG. 2, the first dark period. After the vane 42 is rotated out of the emitted light, the second filter enters the optical path and initially filters light at a wavelength corresponding to point B. As the second filter continues its rotation, the wavelength of the filtered light varies or is swept from point B to point C along line L2 at which time the second filter 38 is substantially perpendicular to the optical path. The vane 42 on the next successive filter 38 then begins entering and interrupting the emitted light to cause the second dark period. When this vane 42 rotates out of the optical path, the third filter enters the emitted light path, and, in a manner identical to that for the first and second filters, passes light beginning at point C and sweeps the wavelength of the light upward to point D along the line L3. This sequence is continuously repeated as the filter assembly 34 is rotated.

As can be seen, the filters 38 are selected such that the wavelength of the filtered light incident on the sample drawer 16 passes through three bandwidths, A–B, B–C, and C–D, which occupy adjacent portions of the infrared spectrum with a period of darkness interjacent each period of irradiation.

When a grain sample, located in the cavity 20, is irradiated with the filtered light, a fraction of the light energy incident on the sample is absorbed, another fraction, depending upon the optical characteristics of the sample and its thickness, is transmitted through the sample, and the remaining fraction is reflected. A portion of the reflected light is detected by the photosensors 44 which provide a voltage indication of the reflected light as the wavelength of the irradiating light sweeps across the infrared spectrum.

The percentage determination of the concentration of moisture and protein is effected by the control and computational functional blocks shown in FIG. 1. Details of the internal operation of these blocks may be had by reference to the aforementioned patents incorporated herein by reference.

A logic unit 52 is provided to generate various control signals in response to the rotational position of the filter assembly 34. The logic unit 52 accepts a "position count" and a "reset" pulse input from a rotation/pulse transducer 48 connected to the filter assembly shaft 40. The transducer 48 provides a series of pulses (e.g. 1000/rev.) as the shaft 40 rotates and a reset pulse signal after each complete revolution. These pulses are counted and decoded in the logic unit 52 to provide appropriately sequenced "sample" signals to sample-and-hold circuits 72, 74; 82a, b, and c; and a "dark period" signal to a sensor amplifier unit 46 once each revolution of the filter assembly 34.

The output of the photosensors 44 is inputted to the sensor amplifier unit 46 which also receives the "dark period" control signal from the logic unit 52. The sensor amplifier unit 46 amplifies the output of the photosensors 44 during both the periods of irradiation and the periods of darkness. Under the control of the "dark period" signal, the sensor amplifier unit 46 compensates the photosensor 44 output during the period of irradiation with the output during the period of darkness. Thus, the output of the sensor amplifier 46 takes into account the response of the photosensors 44 during the dark period, which output may change with time and changing environmental conditions, by adjusting the output during the periods of irradiation by an amount which is representative of the preceding dark period output.

The output of the sensor amplifier 46 is connected to the input of a logarithmic amplifier 70 which is designed to take the common lagarithm of the sensor amplifier 46 output. The logarithmic output is then connected to the selectively operable sample and hold circuits 72 and 74, both of which are adapted to receive their respective "sample" signals from the logic unit 52 which issues these signals as a function of the filter assembly position. The values sampled are voltages representative of the optical density of the sample at the characteristic frequencies for water and the optical density for the characteristic and neutral frequencies of protein.

The respective outputs of the sample and hold circuits 72 and 74 are connected to the inputs of a differential amplifier 80 which produces an output representing the difference between the value stored in each of the sample and hold circuits 72 and 74 at any given time. This difference output is represented by the expression Log $(I_r)_1$ − Log $(I_r)_2$ which is directly proportional to the $\Delta OD$. The output of the differential amplifier 80 is connected to the inputs of the sample and hold circuits 82a, 82b, and 82c. While three sample and hold circuits 82a, b, and c have been shown in FIG. 1, the number of sample and hold circuits required depends upon the total number of $\Delta OD$ values to be stored for subsequent use in computing the percentage values of the desired constituents. In the case of the preferred embodiment, the sample and hold circuit 82a is designed to store the $\Delta OD$ value for the characteristic wavelengths for moisture; the sample and hold circuit 82b is designed to store the $\Delta OD$ value for the characteristic wavelengths for protein; and the sample and hold circuit 82c is designed to store the $\Delta OD$ value for the neutral wavelengths for protein.

As the filter assembly 34 rotates, the logic unit 52 supplies two spaced "sample" signals to the sample and hold circuits 72 and 74 causing these circuits to sample the optical density values for two spaced points in the infrared spectrum. The difference of the common logarithm of these two values is computed by the differential amplifier 80 and thereafter stored in one of the sample and hold circuits 82 as determined by an appropriately supplied control signal from the logic unit 52. As the filter wheel 34 continues its rotation, additional optical density values, representative of the wavelengths of the remaining values, are measured and sampled, their logarithmic difference is computed, and the resultant value stored in the remaining sample and hold circuits 82.

The outputs of the sample and hold circuits 82a, b and c are connected, respectively, to calibration units 92a, 92b, and 92c with the outputs of these calibration units connected to a computing and display unit 94. Each of the calibration units, as described in the aforementioned patents incorporated herein by reference, is provided to correct for possible voltage drift and other irregularities or instabilities which can occur in analog electronic circuits by re-establishing a correlation between the output of the instrument and the various values measured with respect to the standard sample. Each calibration unit introduces a correction factor "C" into the $\Delta OD$ value stored in the associated sample and hold circuit. The output of each calibration unit, represented by C·$\Delta OD$, is then supplied to the computing and display unit 94 for subsequent processing.

Figure 3:
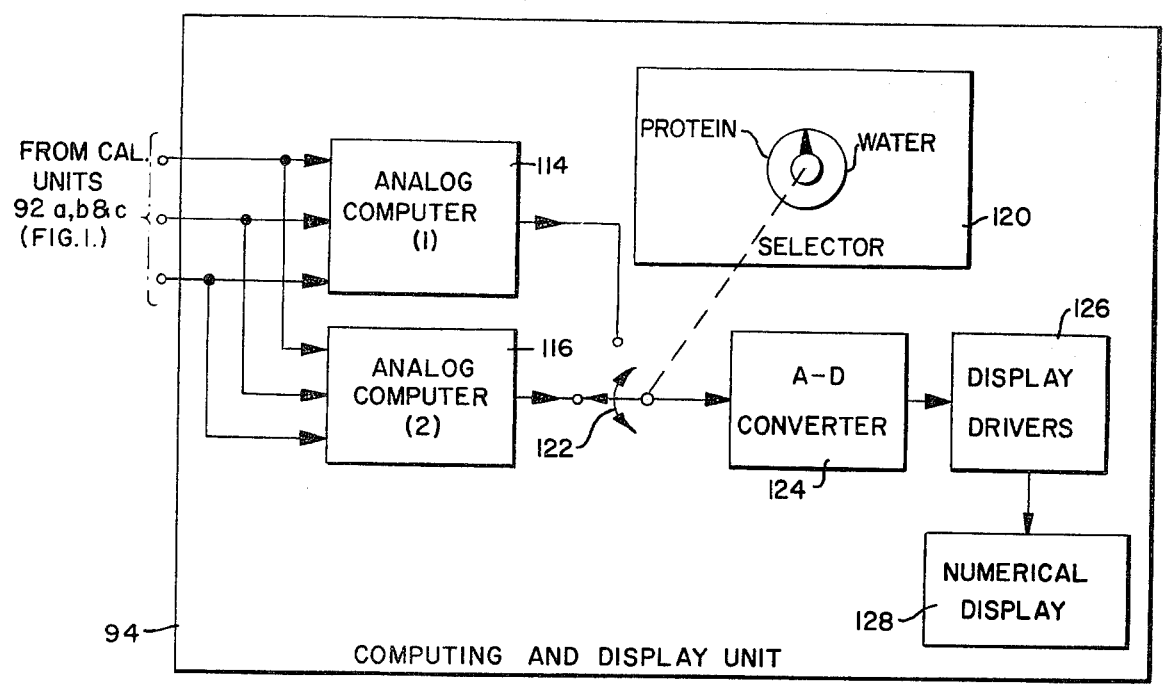
FIG. 3 is a functional block diagram of a computation and display unit.

As shown in FIG. 3, the computing and display unit 94 includes two analog computing units 114 and 116 for computing the percentage value of water and protein. Each of the computer circuits contains standard preprogrammed analog-type circuitry for calculating the percentages of the corresponding constituents using the information stored in the sample and hold circuits 82a, 82b, and 82c and corrected by the corresponding calibration units 92a, 92b and 92c.

An output selector 120 is mechanically connected to a rotary switch 122 to selectively connect one of the outputs of the computer circuits 114 and 116 to an analog-to-digital (A/D) converter 124. The output of the converter 124 is connected to digit display drivers 126 which in turn connects to a numerical display 128 which may take the form, for example, of a Nixie (trademark) tube digit-display or a seven-segment LED display.

Figure 5:
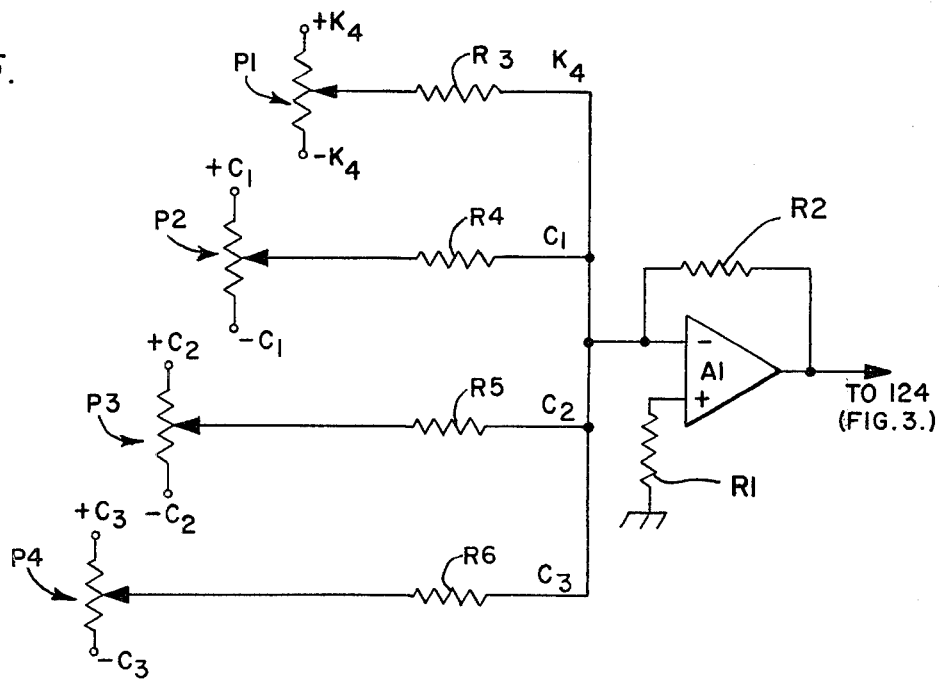
FIG. 5 is a schematic diagram of a scaled summing amplifier sutiable for computing the percentage concentration of oil and moisture in a grain sample.
Figure 6:
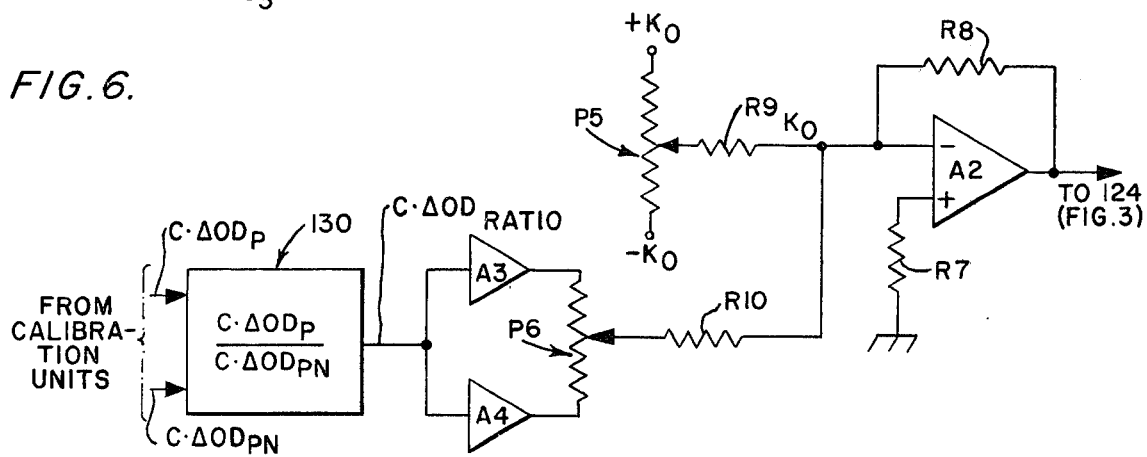
FIG. 6 is a schematic diagram of a scaled summing amplifier circuit sutiable for computing the percentage concentration of protein in a grain sample.

Circuitry for effecting the computation of the moisture percentages in accordance with a variation of equation 6 is shown in schematic form in FIG. 5, and circuitry for effecting the computation of the protein percentage in accordance with the present invention is shown in FIG. 6.

FIG. 5 discloses a scaled-summing amplifier circuit which includes an operational amplifier A1 having a positive input connected through a resistor R1 to ground and a gain-controlling feedback resistor R2 connected between the negative input and the output of the amplifier A1. The negative input is also connected to a scaled resistor-network which includes resistors R3, R4, R5, and R6, each of which has one end connected to the negative input of the amplifier A1 and their other ends connected, respectively, to the tap connection of variable resistors or trim pots P1, P2, P3, and P4.

The end terminals of the trim pot P1 are connected across a voltage potential representing plus $K_4$ and minus $K_4$ values; the end terminals of the trim pot P2 are connected across a voltage potential representative of the plus and minus values of $C_a \cdot \Delta OD$ (from the moisture characteristic wavelength) supplied by the calibration unit 92a from the sample and hold circuit 82a; the end terminals of the trim pot P2 are connected across the voltage potential representative of the plus and minus values of $C_b \cdot \Delta OD$ (from the protein characteristic wavelength) supplied by the calibration unit 92b from the sample and hold circuit 82b; and the end terminals of the trim pot P3 are connected across a voltage potential representative of the plus and minus values of $C_c \cdot \Delta OD$ (from the protein neutral wavelength) supplied by the calibration unit 92c from the sample and hold circuit 82c. The voltage potential for the plus and minus $K_4$ values may be obtained, e.g., from a plus and minus type power supply, and the plus and minus values of the various $C \cdot \Delta OD$ values may be obtained by connecting the output of the calibration units to two unity-gain linear amplifiers, one of which functions as a voltage follower and the other of which functions as an inverter. The end connections of the respective trim pots are then connected across the output of these amplifiers. By adjusting the position of the variable tap of each of the trim pots and selecting appropriate values for the resistors R2, R3, R4, R5, and R6 in accordance with the known operating characteristics of scaled-summing amplifier circuits, the various "influence factors" "K", can be combined with the various $C \cdot \Delta OD$ values to compute the percentage moisture. The circuit of FIG. 5 computes the percentage moisture in accordance with Equation 6, but substitutes the corrected $\Delta OD$ at the protein neutral frequency for the $\Delta OD$ at the oil characteristic frequency. The substitution, in practice, does not significantly diminish the accuracy of the moisture measurement.

FIG. 6 illustrates a circuit suitable for computing the percentage of the protein in accordance with equation 9 of the present invention. The circuit includes an operational amplifier A2 having its positive input connected through a resistor R7 to ground and a gain-controlling feedback resistor R8 connected between the negative input and the output of the amplifier A2. The negative input is also connected to a scaling-resistor network which includes a resistor R9 and a resistor R10. Each of these resistors are connected to a tap terminal of, respectively, a trim pot P5 and another trim pot P6. The trim pot P5 has its fixed ends connected across a voltage potential representative of the plus and minus values of the constant $K_o$ in a manner similar to that for the trim pot P1 of FIG. 5 and the trim pot P6 has its end terminals connected across a voltage potential representative of plus $C \cdot \Delta OD_{ratio}$ and minus $C \cdot \Delta OD_{ratio}$. The value of the $\Delta OD_{ratio}$ represents the quotient of $C \cdot \Delta OD_p$ at the protein characteristic wavelengths and $C \cdot \Delta OD_{pn}$ at the protein neutral wavelengths. This ratio is provided by a computing element 130 which has as its inputs the $C \cdot \Delta OD_p$ value from the computing unit 92c and the $C \cdot \Delta OD_{pn}$ value from the computing unit 92n. The computing element 130, in the preferred form, may be of the type manufactured by the Analog Devices Corporation and identified as Model 433b. The output of the computing element is connected to one side of the trim pot P6 through an unity-gain inverting linear amplifier A3 and the other side of the trim pot P6 through a unity-gain linear amplifier A4 (non-inverting). By adjusting the position of the taps on the trip pots P5 and P6 and selecting appropriate values for the resistors R8, R9, and R10 in accordance with the known operating characteristics of scaled-summing amplifier circuits, the various "influence factors", K, can be combined with $C \cdot \Delta OD_{ratio}$ to compute the percentage protein in accordance with equation 9 of the present invention.

The constant or "influence factors" in equations 5 and 9 vary depending on the type of agricultural product or commodity being tested. The appropriate values for these constants can be ascertained by obtaining $\Delta OD$ readings for various samples of a selected type of grain or agricultural commodity and then subjecting the samples to the standard laboratory analysis to determine the percentages of moisture, oil, and protein in the test sample. The three equations used to determine the percentage content of moisture, protein, and oil are then set equal to their analytically determined values and the resulting simultaneous linear equations solved to arrive at the values of the constants which are then established in the computing circuitry by proper adjustment of the trim pots and selection of the resistance values of the associated resistors in the scaled-summing amplifier circuits.

Figure 4:
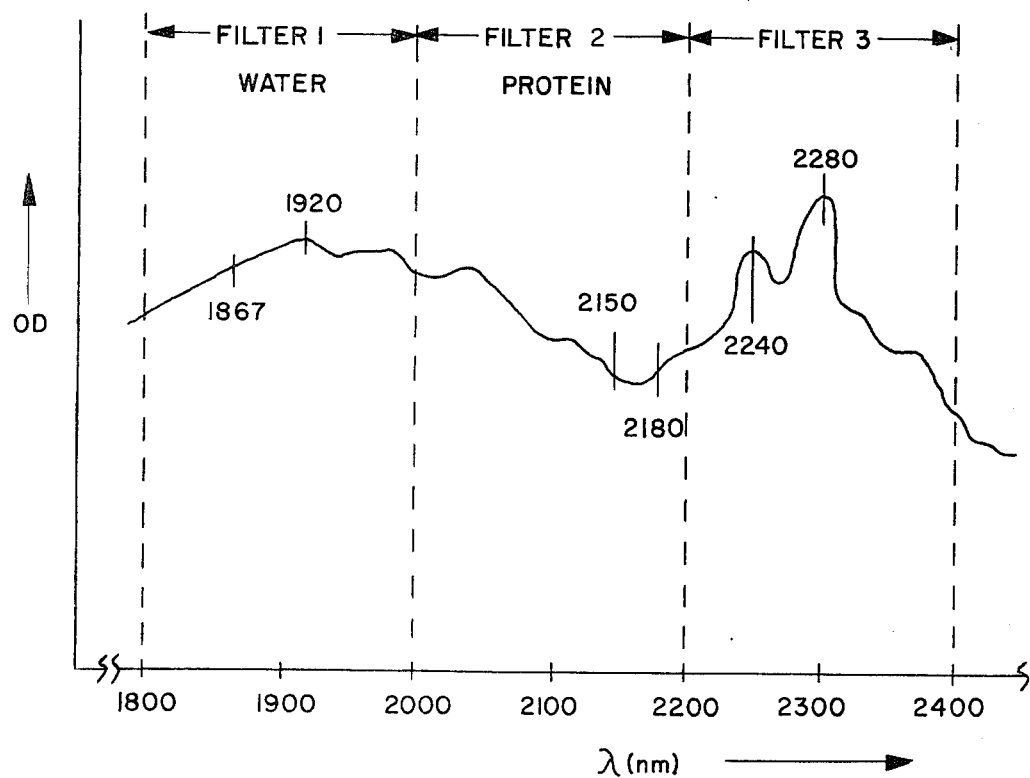
FIG. 4 is an idealized graphical representation of the optical density characteristics of an exemplary grain sample in which the vertical axis represents the qualatitive optical density and the horizontal axis quantatively represents the wavelength of the irradiating light in nanometers (nm)

The characteristic wavelengths and the neutral wavelength at which the $\Delta OD$ value is measured depends upon the type of product being tested. A graph of the optical density of a typical grain sample is shown in FIG. 4 with the horizontal axis representing the wavelength in nanometers (nm) and the vertical axis qualitatively representing optical density. For calculating the $\Delta OD$ value corresponding to the contribution to the reflective spectra by the water content of the grain sample, the $\Delta OD$ at 1867 nm and 1920 nm is calculated. For protein, the $\Delta OD$ at 2150 and 2180 nm (the characteristic wavelength) and 2240 and 2288 (the protein neutral wavelengths) are measured. The optical density values for the various characteristic and neutral wavelengths are sampled by appropriately programming the decoder in the logic unit 52 so that the "sample" control signals issued to the sample and hold circuits 72 and 74 are synchronized with the rotation of the filter assembly 34 such that the selected wavelengths are passed by one of the filters at the time the "sample" control signals are issued.

The equipment described herein is not restricted nor limited to the testing of agricultural commodities nor the determination of the percentage values of moisture and protein in agricultural commodities. The apparatus may be adapted to measure any photo-optically determinable characteristic of a wide variety of materials suitable to this type of analysis and the frequency emission range of the light source and the frequencies filtered by the various filters may be changed to include, in addition to the infrared region, the visible-light spectrum and the ultra-violet light spectrum.

While the computing apparatus has been described as an analog arrangement, the computing may also be effected by the digital logic elements including registers, counters, and suitably programmed arithmetic and logic units (ALU).

In the present invention, the various constants $K_0$–$K_{11}$ utilize the equations are established by suitable adjustment and selection of resistance and voltage values. Flexibility may be obtained by using a set of input "plug-in" printed circuit cards with each card having a different set of resistance determined voltage values. The cards may be equipped with edge connectors for ready insertion and removal from strip type connectors associated with the apparatus.

The invention described above may be embodied in other specific forms without departing from the spirit or scope thereof. The present embodiments are therefore to be considered in all respects as illustrative and non-restrictive, the scope of the invention being indicated by the appended claims and their legal equivalent.

I claim:

1. A photo-optical analyzer for optically determining a value representative of the percentage protein in an agricultural product test sample, said analyzer comprising:

means for irradiating an agricultural product test sample with light energy the wavelength of which sweeps across a preselected wavelength range including a sub-range in which the optical density of the test sample is known to vary as a function of the percentage protein in the test sample and another preselected sub-range in which the optical density of the sample is known to be substantially independent of the percentage protein in the sample;

light responsive means positioned to detect a portion of the light energy after having irradiated the test sample;

computational means connected to said light responsive means for determining a value representative of the percentage protein in the test sample including means for computing a ratio of the difference between the common logarithm of the optical density at first and second spaced points in said first-mentioned sub-range to the difference between the common logarithm of the optical density at first and second spaced points in said second-mentioned sub-range.

2. A photo-optical analyzer claimed in claim 1, wherein:

said light responsive means is positioned to detect light energy reflected from said test sample.

3. The photo-optical analyzer claimed in claim 1, wherein said means for irradiating comprises:

means for irradiating a test sample with light energy, the wavelength of which cyclically sweeps across a selected band width including the first and second-mentioned wavelength sub-ranges.

4. The photo-optical analyzer claimed in claim 3, wherein said means for irradiating further comprises:

a wide-band emission light source adapted to direct a portion of its light energy along an optical path towards the test sample; and variable filter means insertable into the optical path and operable to pass light energy, the wavelength of which sweeps across the selected band width.

5. The photo-optical analyzer claimed in claim 4, wherein said variable filter means further comprises:

a narrow band filter insertable into said optical path at a first angular orientation; and means for changing the angular orientation between said filter and said optical path from said first angular orientation to a second angular orientation, said filter transmitting light energy across said selected band width while said angular orientation is changing.

6. The photo-optical analyzer claimed in claim 5, wherein said narrow band filter further comprises:

a plate-like filter means attached at one end to a rotatable shaft, the filter entering said optical path at a first angular orientation in response to the rotation of said shaft and changing to said second angular rotation relative said optical path to effect the change in wavelength.

7. The photo-optical analyzer claimed in claim 6, further comprising:

logic control means position synchronized with the rotation of said shaft and adapted to provide control signals when said test sample is irradiated with light energy at the first and second spaced points in said first-mentioned sub-range and the first and second spaced points in said second-mentioned sub-range.

8. The photo-optical analyzer claimed in claim 6, wherein said plate-like filter means further comprises:

a plurality of variable plate-like filters attached at one end thereof to a rotatable shaft, said filters successively entering said optical path at a first angular orientation in response to rotation of said shaft and changing to a second angular rotation relative said optical path with continued rotation of said shaft, each of said plural filters having a different narrow transmission frequency such that said test sample is irradiated with light, the wavelength of which varies in adjacent band widths to define, in a composite manner, said first-mentioned band width.

9. The photo-optical analyzer claimed in claim 1, wherein:

said computational means includes means for determining a value representative of the percentage protein concentration in accordance with the following equation:

$$\text{protein } \% = K_0 + K_1 \frac{\log \frac{1}{R_{1c}} - \log \frac{1}{R_{2c}}}{\log \frac{1}{R_{1n}} - \log \frac{1}{R_{2n}}} = K_0 + K_1 \frac{\Delta OD_c}{\Delta OD_n}$$

in which the constants $K_o$ and $K_1$ are predetermined values, R represents the light energy reflected from the test sample, and the subscripts 1 and 2 represent the first and second spaced apart points in said first-mentioned sub-range and in said second-mentioned sub-range.

10. The photo-optical analyzer claimed in claim 9, wherein said computational means further comprises:

logarithmic amplifier means connected to the output of said light responsive means;

sample and hold circuits for storing voltage values representative of the common logarithm of the first and second spaced points in said first and second-mentioned sub-ranges;

differential amplifier circuit means for generating the difference between the common logarithm of said voltage values between said first and second spaced points in said first and second-mentioned sub-ranges; and circuit means for computing said ratio of said logarithm difference with at least one constant to provide a percentage indication of the protein in said sample.

11. The photo-optical analyzer claimed in claim 9, wherein said computational means further comprises:

means for determining a value of the optical density at first and second spaced points in a third sub-range in which the optical density is known to vary as a function of the percentage moisture in the test sample and for computing a value representative of the percentage moisture in the test sample as a function of selected ones of the optical density values determined from measurements in said first, second, and third sub-ranges.

12. The photo-optical analyzer claimed in claim 1, wherein:

the first and second points in said first-mentioned sub-range are 2150 nm and 2180 nm.

13. The photo-optical analyzer claimed in claim 1, wherein:

the first and second points in said second-mentioned sub-range are 2240 nm and 2280 nm.

* * * * *